(12) United States Patent
Coskun et al.

(10) Patent No.: US 12,315,215 B2
(45) Date of Patent: May 27, 2025

(54) INDICATION SYSTEM FOR A SURGICAL LIGHTING APPARATUS

(71) Applicant: TRUMPF MEDIZIN SYSTEME GMBH + CO. KG, Saalfeld (DE)

(72) Inventors: Tayfur Coskun, Saalfeld (DE); Nick Neuendorf, Saalfeld (DE); Andreas Huber, Saalfeld (DE)

(73) Assignee: TRUMPF MEDIZIN SYSTEME + CO. KG, Saalfeld (DE)

( * ) Notice: Subject to any disclaimer, the term of this patent is extended or adjusted under 35 U.S.C. 154(b) by 320 days.

(21) Appl. No.: 17/705,541

(22) Filed: Mar. 28, 2022

(65) Prior Publication Data

US 2022/0327801 A1 Oct. 13, 2022

(51) Int. Cl.
*G06V 10/60* (2022.01)
*A61B 90/30* (2016.01)
*G06V 10/82* (2022.01)

(52) U.S. Cl.
CPC .............. *G06V 10/60* (2022.01); *A61B 90/30* (2016.02); *G06V 10/82* (2022.01)

(58) Field of Classification Search
CPC ........ G06V 10/60; A61B 90/30; A61B 34/25; A61B 90/361
See application file for complete search history.

(56) References Cited

U.S. PATENT DOCUMENTS

| | | | |
|---|---|---|---|
| 8,134,307 B2 * | 3/2012 | Fontijn | H05B 47/19 315/307 |
| 8,292,804 B2 | 10/2012 | Marka et al. | |
| 9,491,835 B2 | 11/2016 | Elfring et al. | |
| 9,638,406 B1 | 5/2017 | Liang et al. | |
| 10,271,398 B2 | 4/2019 | Hollopeter et al. | |
| 10,383,195 B2 | 8/2019 | Hartl et al. | |
| 10,548,672 B2 | 2/2020 | Yang et al. | |
| 10,610,409 B2 | 4/2020 | Bacher et al. | |
| 10,767,822 B2 | 9/2020 | Munari | |
| 10,828,124 B2 | 11/2020 | Geerlings et al. | |

(Continued)

FOREIGN PATENT DOCUMENTS

| | | | |
|---|---|---|---|
| DE | 20315225 U1 | 3/2005 | |
| DE | 102008041284 A1 * | 11/2009 | ............... A61B 3/13 |

(Continued)

OTHER PUBLICATIONS

Curlin J, Herman CK. Current State of Surgical Lighting. Surg J (N Y). Jun. 19, 2020;6(2):e87-e97. doi: 10.1055/s-0040-1710529. PMID: 32577527; PMCID: PMC7305019. (Year: 2020).*

(Continued)

*Primary Examiner* — Michael Robert Cammarata
(74) *Attorney, Agent, or Firm* — Barnes & Thornburg LLP

(57) ABSTRACT

An indication system for a surgical lighting apparatus is provided, comprising a computer device connectable to a plurality of light modules, wherein the computer device is configured to determine an illumination setting for each of the plurality of light modules; compare the illumination settings of at least two of the plurality of light modules to at least one output illumination threshold; and output an indication if the at least one output illumination threshold is exceeded. A surgical lighting apparatus, a method of indication, and a detection system for a surgical lighting apparatus are also provided.

17 Claims, 10 Drawing Sheets

(56) References Cited

U.S. PATENT DOCUMENTS

| | | | |
|---|---|---|---|
| 10,904,973 B2* | 1/2021 | Sattler | |
| 2004/0129860 A1* | 7/2004 | Thubaud | |
| 2007/0138966 A1* | 6/2007 | Marka | A61B 90/30 |
| | | | 315/76 |
| 2008/0232086 A1* | 9/2008 | Marka | H05B 47/18 |
| | | | 362/85 |
| 2009/0261759 A1* | 10/2009 | Fornasiero | H05B 47/165 |
| | | | 315/307 |
| 2015/0035440 A1* | 2/2015 | Spero | F21S 41/147 |
| | | | 315/153 |
| 2015/0208478 A1* | 7/2015 | Sattler | A61B 90/30 |
| | | | 315/151 |
| 2016/0174336 A1* | 6/2016 | Elfring | F21V 23/0471 |
| | | | 315/153 |
| 2017/0030573 A1 | 2/2017 | Alexanderson et al. | |
| 2017/0167702 A1 | 6/2017 | Mariampillai et al. | |
| 2017/0318644 A1* | 11/2017 | Hartl | H05B 47/115 |
| 2018/0124892 A1* | 5/2018 | Hollopeter | H05B 47/155 |
| 2018/0231227 A1 | 8/2018 | Strlin | |
| 2018/0347805 A1* | 12/2018 | Abou-Fadel | G06F 1/1632 |
| 2020/0329544 A1* | 10/2020 | Göergen | H05B 47/10 |
| 2021/0007810 A1* | 1/2021 | Rainis | |
| 2021/0113292 A1* | 4/2021 | Ueda | G02B 21/36 |
| 2021/0220076 A1* | 7/2021 | Takemoto | H05B 47/105 |
| 2021/0307145 A1* | 9/2021 | Oelgarth | A61B 90/35 |

FOREIGN PATENT DOCUMENTS

| | | | | |
|---|---|---|---|---|
| DE | 102008034827 A1 * | 2/2010 | | A61B 5/01 |
| EP | 2912405 B1 | 10/2017 | | |
| EP | 3556318 A1 | 10/2019 | | |
| WO | 2020087542 A1 | 5/2020 | | |

OTHER PUBLICATIONS

Ali, Shahnewaz, et al. "Supervised scene illumination control in stereo arthroscopes for robot assisted minimally invasive surgery." IEEE Sensors Journal 21.10 (2020): 11577-11587. (Year: 2020).*

European Search Report in Related Application EP24197061.5, Sep. 30, 2021, 8 pages.

European Search Report in Related Application EP21166456.0, Sep. 23, 2024, 8 pages.

* cited by examiner

INDICATION SYSTEM FOR A SURGICAL LIGHTING APPARATUS

CROSS-REFERENCE TO RELATED APPLICATIONS

This application claims the benefit of European Patent Application Serial No. 21166456.0, filed Mar. 31, 2021, the entire disclosure of which is incorporated herein by reference in its entirety.

TECHNICAL FIELD

The present disclosure relates to an indication system for a surgical lighting apparatus. In particular, the disclosure relates to an indication system comprising a computer device connectable to a plurality of light modules. The disclosure further relates to a system for determining overlap of illumination zones of surgical lighting apparatus.

BACKGROUND

Surgical lights are used in operating rooms to illuminate the field of surgery. IEC60601-2-41 states that total irradiance should be minimized, that the total irradiance in the lighted area should not exceed a specified amount, that it is possible to exceed that irradiance amount if the user overlaps light fields of several luminaires such as light modules, and that this information should be included in the instructions for use (IFU), so that users can act accordingly. This creates certain tasks and obligations on the user. It is desired to further aid the user in such tasks.

SUMMARY OF THE DISCLOSURE

The present disclosure includes one or more of the features recited in the appended claims and/or the following features which, alone or in any combination, may comprise patentable subject matter, including, in some embodiments, an indication system for a surgical lighting apparatus, a surgical lighting apparatus, and a method of indication, as defined in the appended claims, to which reference should now be made.

According to a first aspect of the present disclosure, there is provided an indication system for a surgical lighting apparatus. The indication system comprises a computer device connectable to a plurality of light modules. The computer device is configured to: determine an illumination setting for each of the plurality of light modules; compare the illumination settings of at least two of the plurality of light modules to at least one output illumination threshold; and, output an indication if the at least one output illumination threshold is exceeded.

It has been found that providing an indication if the at least one output illumination threshold is exceeded provides users such as surgeons with a better user experience. In particular, such an indication allows easier compliance with international surgical lighting standard IEC60601-2-41. As set out above, this standard determines the requirements of lighting techniques of surgical lamps, and prescribes that the user should be informed if overlapping of light modules of a surgical lighting apparatus may result in an amount of irradiance, or power, or luminance, being exceeded.

The indication system of the present disclosure draws additional attention to the information, but only if the at least one output illumination threshold is exceeded. Thus, the indication system provides guided interaction between the user and the indication system, and is efficient as the indication system only draws additional attention when a threshold is exceeded.

In some embodiments, the computer device is configured to: if the plurality of light modules comprises more than two light modules, determine the two of the plurality of light modules having the two highest illumination settings. By determining the two light modules having the two highest illumination settings, it may be determined, using only the illumination settings of these two light modules, whether at least one output illumination threshold is exceeded. This provides improved computational efficiency and prevents unnecessary indications.

In some embodiments, the step of comparing the illumination settings of at least two of the plurality of light modules to at least one output illumination threshold may comprise: combining the illumination settings of the at least two of the plurality of light modules, or of the two of the plurality of light modules having the two highest illumination settings, and comparing the combined illumination setting to a total output illumination threshold. By combining the illumination settings of (some of) the light modules, only a single comparison to a total output illumination threshold is required to determine if an indication should be output.

The illumination setting for each of the plurality of light modules may be a percentage of maximum illumination of the light module, e.g. 50% of maximum illumination, or it may be a set power (e.g. irradiance) of the light module, e.g. 160 kilolux (klx) or 615 W per m$^2$.

The total output illumination threshold may be a percentage of a total illumination setting of the light modules. For example, the total output illumination threshold may be 160% of the maximum illumination of each light module, e.g. two light modules each set to an illumination setting of 80%. Alternatively, the total output illumination threshold may be an irradiance, such as 256 klx, or 260 klx, or 180 klx, or 205 klx.

The computer device may be configured to convert a determined illumination setting to a different unit, so that the determined illumination setting and the output illumination threshold align. For example, if the illumination setting for each of the plurality of light modules is determined as a percentage of maximum illumination of the light module, and the threshold is an irradiance, the computer device may convert the percentage of maximum illumination to an irradiance, and vice versa.

In some embodiments, the step of comparing the illumination settings of at least two of the plurality of light modules to at least one output illumination threshold may comprise: comparing an illumination setting of a first one of the plurality of light modules to a first output illumination threshold, and an illumination setting of a second one of the plurality of light modules to a second, dynamic, output illumination threshold, the second threshold being dependent on at least one of the first threshold and the first illumination setting. By comparing a first illumination setting to a first output illumination threshold, and a second illumination setting to a second, dynamic, output illumination threshold, it may be ensured that a combined illumination setting does not exceed a threshold without having to calculate the combined illumination setting.

In some further embodiments, the first one and the second one of the plurality of light modules may be the two of the plurality of light modules having the two highest illumination settings.

In some embodiments, the computer device may be configured to determine whether an illumination zone of one of the plurality of light modules overlaps with an illumination zone of another one of the plurality of light modules.

In some further embodiments, the computer device may be configured: not to output the indication if the illumination zones do not overlap; and/or to output a further indication if the illumination zones do overlap and the output illumination threshold is exceeded; and/or to output the indication only if the illumination zones overlap. By determining if illumination zones overlap, indications may further be reduced to necessary indications only, thus providing a more efficient and more user friendly system, or providing a further indication if the illumination zones are overlapped, such that up-to-date indications may be provided.

In some further embodiments, the computer device may be configured to continually determine if the illumination zones overlap. This allows for up-to-date indications to be provided. Alternatively, the computer device may be configured to determine if the illumination zones overlap at predetermined time intervals. The predetermined time interval may be between 1 second and 1 minute, or between 1 second and 10 seconds, or between 1 second and 5 seconds. Increasing the time interval may reduce the computational burden, and therefore increase the efficiency of the system.

In some further embodiments, the computer device may be configured to determine a percentage overlap if the illumination zones overlap. Such a percentage overlap may help in providing an indication only when required. That is, an indication may only be provided if the overlap exceeds e.g. 5%, or 10%, or 20%, or 30%, or any other suitable value.

In some further embodiments, each one of the plurality of light modules comprises at least one of: a structured light system, and the step of determining whether the illumination zones overlap comprises detecting an interference pattern of structured light of the structured light systems; and a camera, and the step of determining whether the illumination zones overlap comprises comparing images of each of the cameras for corresponding features. As will be appreciated, the illumination zones are considered to overlap if either the interference pattern of structured light, or corresponding features of the camera images, are within each of the respective illumination zones. This allows for efficient detecting of overlapping illumination zones, including a percentage of overlap if required, using relatively simple structured light systems, or widely available cameras, such as standard RGB cameras using a CCD or CMOS sensor.

In some further embodiments, the computer device further comprises an artificial neural network, configured using a training set of data, wherein: the step of detecting the interference pattern comprising using the artificial neural network to detect the interference pattern of the structured light; and/or the step of comparing images of each of the cameras for feature detection comprises using the artificial neural network to detect corresponding features in images of different cameras.

Using an artificial neural network allows for improved detecting of overlap. Further, the system comprising cameras and structured light systems, and the artificial neural network being used to detect interference patterns and corresponding features, may further improve detecting of overlap.

Where provided, the artificial neural network may be configured to receive and process context-sensitive information based on at least one of: a patient characteristic; a surgery type; environmental data; and illumination settings, and/or focus settings, of the at least two light modules. Using context-sensitive processing allows for e.g. an output illumination threshold to be dynamic, based on at least one patient characteristic (e.g. a lower threshold based on the patient body type and/or skin pigmentation), on surgery type (e.g. a higher threshold based on the specific surgical procedure), or on other data.

In some further embodiments, the computer device may be configured to prevent an illumination setting of one of the plurality of light modules being changed until the indication has been acknowledged.

In some embodiments, in which the artificial neural network is used, the computer device may be configured to automatically reduce an illumination setting of one of the plurality of light modules if the at least one output illumination threshold is exceeded. The illumination setting may be automatically reduced only after the at least one output illumination threshold is exceeded for a predetermined period of time and/or by a predetermined illumination setting amount and/or upon the indication not being acknowledged within a predetermined period of time.

In some embodiments, it may be determined if the illumination zones of light modules overlap before comparing the illumination settings of at least two of the plurality of light modules to at least one output illumination threshold. As such, the illumination settings may only be compared with at least one output illumination threshold if the illumination zones overlap.

In some embodiments, the illumination settings of at least two of the plurality of light modules are compared to at least one output illumination threshold before determining if the illumination zones of light modules overlap. As such, the determination of an overlap may only be performed if the output illumination threshold is exceeded.

In alternative embodiments, each one of the plurality of light modules may comprise at least one of: a position sensor; an angle sensor; an accelerometer; and a gyroscope, for determining whether an illumination zone of one of the plurality of light modules overlaps with an illumination zone of another one of the plurality of light modules. In this embodiment, the system determines the position and orientation of each light module relative to each of the other light modules to determine whether an illumination zone of one of the plurality of light modules overlaps with an illumination zone of another one of the plurality of light modules.

In further alternative embodiments, the computer device may be connected to a camera system, the camera system comprising at least two cameras for determine a position and an angle of each one of the plurality of light modules, and a position of the illumination zones of each one of the plurality of light modules, for determining whether an illumination zone of one of the plurality of light modules overlaps with an illumination zone of another one of the plurality of light modules.

In some embodiments, the indication system comprises an indicator. The indication may be output by activating the indicator. The indicator may be a visual indicator and/or an audible indicator.

In some embodiments, the indication is output on at least one of: one of the plurality of light modules; a wall control panel; a mobile controller; and a third party device.

In some embodiments, the indication is at least one of a visual indication; and an audible indication. This may allow for an indication to be output clearly, and for it to be quickly received, by a user.

For example, one of, or each of, the light modules may comprise indicia to display the indication. For example, an indication may be displayed by illuminating the indicia. The indicia may be illuminated in specific colour. The colour may be a colour that makes the indication noticeable, e.g. red, yellow or orange.

In some further embodiments, each of the plurality of light modules comprises a light module control panel which comprises the indicia.

The wall control panel may comprise a Graphical User Interface (GUI). The indication may be output within the GUI. Alternatively or additionally, the mobile controller may comprise a, or the, Graphical User Interface (GUI).

In some embodiments, the indication may comprise context-sensitive information such as at least one of: a patient characteristic; surgery type; environmental data; and illumination settings, and/or focus settings, of the at least two light modules. Including such context-sensitive information may provide for improved and/or guided human-machine interaction and may allow the user to easily see relevant context-sensitive information.

In some embodiments, the computer device may be configured to receive at least one of: inputs for acknowledging the indication; inputs for putting the indication system on hold; and inputs for pausing the indication. The inputs for putting the indication on hold may comprise an amount time to put the indication system on hold, or an event to trigger reactivation of the indication system. The event may be: changing the light module output illumination setting; or the detection of movement of the light module. The inputs for delaying the indication may comprise an amount of time to delay the indication, or an event to trigger release of the indication. The event may be: changing the light module output illumination setting; or the detection of movement of the light module. As will be appreciated, the indication may be "paused" only after it has been activated, whereas the indication system may be put on hold at any time. Such inputs allow for a more efficient indication system in which a user may interact with the indication in a number of improved ways.

In some embodiments, the computer device may be configured to receive an input for increasing and/or decreasing an illumination setting of one of, or each of, the plurality of light modules. At least one of the light modules, the wall control panel, and the GUI may comprise inputs for providing the input for increasing and/or decreasing the illumination setting.

In some further embodiments, the computer device may be configured to, each time an illumination setting of one of the plurality of light modules is modified, compare the illumination settings of at least two of the plurality of light modules to at least one output illumination threshold.

The computer device may comprise a processor and memory. The memory may store instructions which, when executed by the processor, enable the indication system to carry out the steps it is configured to execute. If the computer device does not comprise memory, the computer device may be a thin client connected to a server, wherein the server stores the instructions.

According to a second aspect of the present disclosure, there is provided a surgical lighting apparatus comprising: an indication system substantially as described herein; and a plurality of light modules connected to the computer device.

In some embodiments, the surgical lighting apparatus comprises a controller configured to receive an input for increasing and/or decreasing an illumination setting of one of, or each of, the plurality of light modules, said controller being further configured to communicate said input to said computer device of said indication system.

In embodiments where the indication system comprises at least one of the light module, the wall control panel, and the GUI, comprising inputs, the controller may be configured to receive said input for increasing and/or decreasing an illumination setting from said inputs.

In some embodiments, each of the at least two light modules comprises a structured light camera connected to the computer device.

According to a third aspect of the present disclosure, there is provided a method of indication for a surgical lighting apparatus comprising a plurality of light modules, comprising: determining an illumination setting for each of the plurality of light modules; comparing the illumination settings of at least two of the plurality of light modules to at least one output illumination threshold; and, outputting an indication if the at least one output illumination threshold is exceeded.

In some embodiments, the method may comprise the step of: if the plurality of light modules comprises more than two light modules, determining the two of the plurality of light modules having the two highest illumination settings.

In some embodiments, the method may comprise the step of: combining the illumination settings of the at least two of the plurality of light modules, or the two of the plurality of light modules having the two highest illumination settings, and comparing the combined illumination setting to a total output illumination threshold.

In some embodiments, the method may comprise the step of: comparing an illumination setting of a first one of the plurality of light modules to a first output illumination threshold, and an illumination setting of a second one of the plurality of light modules to a second, dynamic, output illumination threshold, the second threshold being dependent on at least one of the first threshold and the first illumination setting. The first one and the second one of the plurality of light modules may be the two of the plurality of light modules having the two highest illumination settings.

In some embodiments, the method may comprise the step of: determining whether an illumination zone of one of the plurality of light modules overlaps with an illumination zone of another one of the plurality of light modules.

In some further embodiments, determining whether the illumination zones overlap may comprise using structured light systems of the plurality of light modules to detect an interference pattern of structured light of the structure light systems.

In some further embodiments, determining whether the illumination zones overlap may comprise using cameras of the plurality of light modules to detect corresponding features in images of different cameras.

In some further embodiments, the step of detecting the interference pattern and/or the step of detecting corresponding features in images of different cameras comprises using an artificial neural network, configured using a training set of data. If both cameras and structured light systems/cameras are used, and the artificial neural network is used in detecting both the interference patterns and corresponding features, detection performance may be improved.

In some further embodiments, using the artificial neural network comprises context-sensitive processing based on at least one of: a patient characteristic; surgery type; environmental data; and illumination settings, and/or focus settings, of the at least two light modules.

The step of determining whether an illumination zone of one of the plurality of light modules overlaps with an illumination zone of another one of the plurality of light modules may be achieved using position sensors, angle sensors, accelerometers, and gyroscopes. Alternatively, this may be achieved using a camera system for determine a position and angle of each of the plurality of light modules.

In some further embodiments, the method may comprise at least one step of: preventing outputting the indication if the illumination zones do not overlap; outputting a further indication if the illumination zones do overlap and the output illumination threshold is exceeded; and outputting the indication only if the illumination zones overlap.

According to a fourth aspect of the present disclosure, there is provided a detection system for a lighting apparatus, comprising: a computer device connectable to a plurality of light modules, wherein the computer device is configured to: determine whether an illumination zone of one of the plurality of light modules overlaps with an illumination zone of another one of the plurality of light modules.

In some further embodiments, each one of the plurality of light modules comprises a structured light system, and the computer device is configured to determine whether the illumination zones overlap comprises detecting an interference pattern of structured light of the structure light systems.

In a further embodiment, the detection system comprises at least two cameras, wherein the step of determining whether the illumination zones overlap comprises comparing images of each of the cameras for corresponding features. The at least two cameras may be provided in respective ones of the plurality of light modules. In one particular embodiment, each light module comprises a camera. As will be appreciated, the illumination zones are considered to overlap if the corresponding features of the camera images are within each of the respective illumination zones.

In some further embodiments, the computer device may be configured to determine a percentage overlap if the illumination zones overlap.

In some further embodiments, the step of detecting the interference pattern comprises using an artificial neural network, configured using a training set of data.

In some alternative embodiments, the plurality of light modules may comprise at least one of a position sensor, an angle sensor, an accelerometer, and a gyroscope, for determining whether an illumination zone of one of the plurality of light modules overlaps with an illumination zone of another one of the plurality of light modules. In alternative embodiments, the computer device may be connected to a camera system, the camera system comprising at least two cameras for determine a position and an angle of each of the plurality of light modules, and a position of the illumination zones, for determining whether an illumination zone of one of the plurality of light modules overlaps with an illumination zone of another one of the plurality of light modules.

Further features of the second, third, and fourth aspects of the present disclosure are described above in relation to the first aspect of the present disclosure.

Where functional components are referred to in apparatus embodiments for carrying out various steps of the described method(s) it will be understood that these components may be implemented in hardware, in software, or a combination of the two. When implemented in hardware, the components may be implemented as one or more hardware components, such as one or more application specific integrated circuits. When implemented in software, the components may be implemented as one or more computer programs that are executed on one or more processors.

It will be appreciated that features described in relation to one aspect of the present disclosure may also be applied equally to all of the other aspects of the present disclosure. Features described in relation to the first aspect of the present disclosure may be applied equally to the second and third aspects of the present disclosure and vice versa. For example, apparatus features described in relation to the first, second, or fourth aspect may be applied, mutatis mutandis, to the method of the third aspect.

Additional features, which alone or in combination with any other feature(s), such as those listed above and/or those listed in the claims, can comprise patentable subject matter and will become apparent to those skilled in the art upon consideration of the following detailed description of various embodiments exemplifying the best mode of carrying out the embodiments as presently perceived.

BRIEF DESCRIPTION OF DRAWINGS

The disclosure will be further described, by way of example only, with reference to the accompanying drawings, in which.

DETAILED DESCRIPTION OF DRAWINGS

Figure 1:
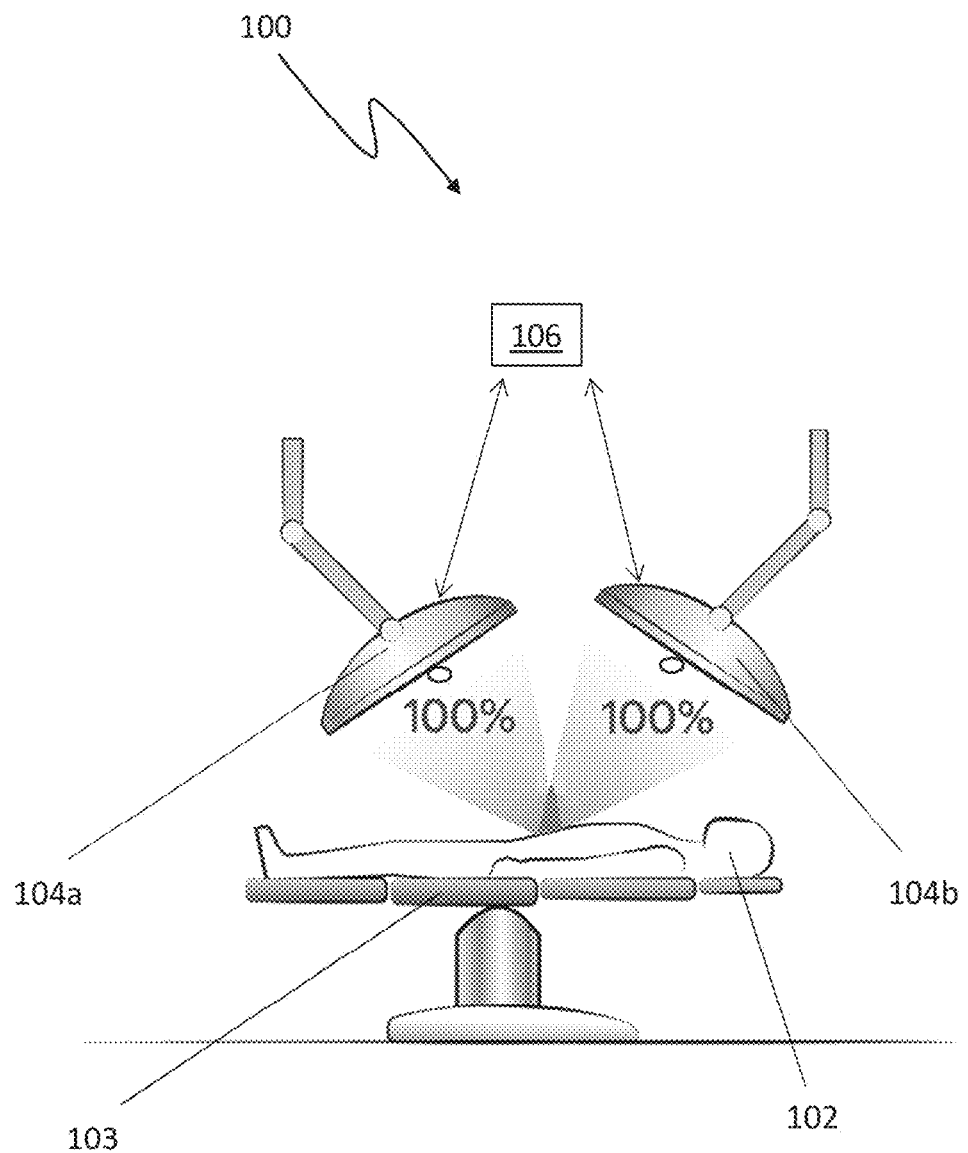
FIG. 1 shows a schematic illustration of an indication system according to a first embodiment.

FIG. 1 shows a schematic illustration of an indication system 100 for a surgical lighting apparatus. The surgical lighting apparatus is configured to illuminate a surgery site on a patient 102 disposed on a patient support apparatus 103.

The indication system 100 is in communication with the surgical lighting apparatus which comprises two light modules 104a, 104b. However, it will be appreciated that the surgical lighting apparatus may comprise three, four, or more such light modules. The indication system 100 comprises a computer device 106 which is connectable to the two light modules 104a, 104b. The connection between the computer device 106 and the light modules 104a, 104b may be wireless or wired. The computer device 106 is configured to receive, or determine, the output illumination setting of each light module 104a, 104b, in the surgical lighting apparatus.

The computer device 106 of the indication system 100 may be a standalone computer device, i.e. a device that is independent from other parts of the surgical lighting apparatus. Alternatively, the computer device 106 may be integral to one of the two light modules 104a, 104b, to a wall control panel connectable to the computer device 106, or to a hospital computer system such as an Electronic Health Record system, or to a third party device such as a tablet.

An indication is sent by the indication system 100 if at least one output illumination threshold is exceeded. The at least one output illumination threshold is exceeded in dependence of an illumination setting of the light modules 104a, 104b. The output illumination threshold may be a single threshold, i.e. the illumination setting of each of the light modules 104a, 104b may be combined so as to calculate a combined illumination setting to be compared to a total output illumination threshold.

For example, if an illumination setting of each of the light modules 104a, 104b is 80%, the combined illumination setting is 160%. If the total output illumination threshold is, e.g., 150%, the threshold is exceeded and an indication is output by the indication system 100.

If the surgical lighting apparatus comprises more than two light modules 104a, 104b, the indication system first determines the two light modules having the two highest illumination settings. For example, if an illumination setting of the first light module 104a is 30%, an illumination setting of the second light module 104b is 80%, an illumination setting of a third light module (not shown) is 90%, and a total output illumination threshold is, e.g., 150%, the threshold is exceeded as the combined illumination setting of the second and third light modules is 170%.

Although the illumination setting values and threshold values in these examples are expressed in percent of maximum illumination of a light module, they may also be expressed in, or converted into or from, irradiance in klx or W per m². Converting between irradiance and percentage illumination settings may include using a lookup table. The lookup table may comprise percentage illumination settings and equivalent irradiance values.

Table 1 shows various examples of illumination settings for surgical lighting apparatuses having one (1 LH), two (2 LH), or three (3 LH) light modules, and whether an indication would be output if a total output illumination threshold is 250 klx and a combined illumination setting of the two light modules having the two highest illumination settings (2 LHmax) is compared to said total output illumination threshold.

80%. This may be compared to a first output illumination threshold, which may be, e.g. 60%. The illumination setting of the second light module 104b may be 80%. This may be compared to a second, dynamic, output illumination threshold which is equal to, e.g. 150% minus the illumination setting of the first light module 104a, so may in this case be 70%. As the illumination settings of the first and second light modules 104a, 104b exceed the first output illumination threshold and the second, dynamic, output illumination thresholds, an indication would be output.

The indication may be communicated to one of, or each of, the light modules 104a, 104b, each of which has a light module control panel. Alternatively or additionally, the indication may be communicated to a Graphical User Interface (GUI) of a wall control panel, of a separate third party device such as a tablet, or the like.

The indication may be output as a visual indication or an audible indication, or it may be output as a combination of a visual and audible indication. There may be multiple visual indications and/or audible indications which make up the indication.

Figure 2:
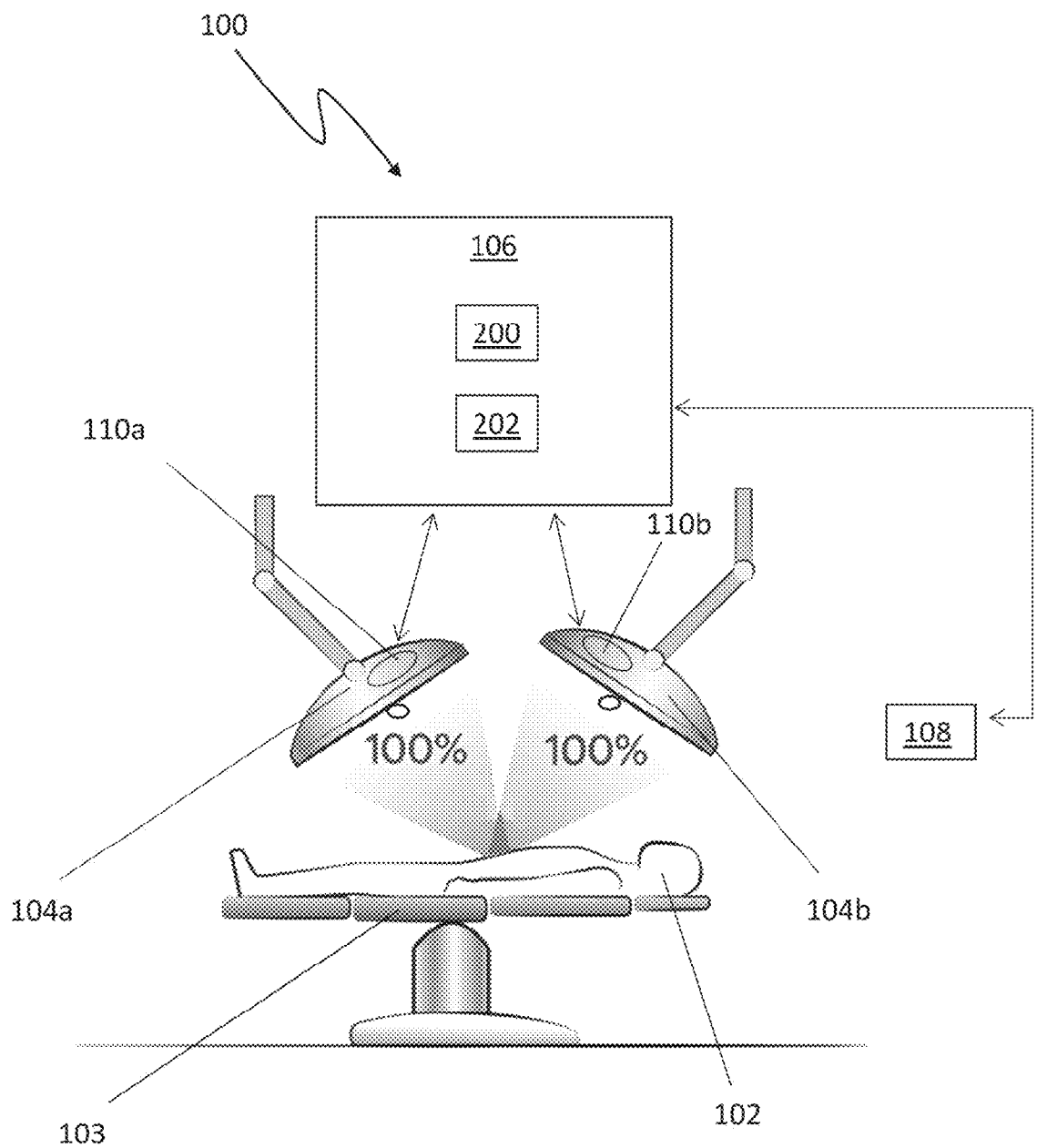
FIG. 2 shows a schematic illustration of a surgical lighting apparatus according to a second embodiment, including an indication system according to a second embodiment.

As shown in FIG. 2, the computer device 106 may comprise a processor 200 and a memory 202. In this example, a wall control panel 108 is shown in communication with the computer device 106; the function of the wall control panel 108 is described above. The wall control panel 108 is configured to display the GUI, which is further described below with reference to FIGS. 10a and 10b. Further, the light modules 104a, 104b, comprise respective light module control panels 110a and 110b; again, the function of the light module control panels 110a, 110b is described below with reference to FIGS. 9a, 9b and 9c.

Figure 3:
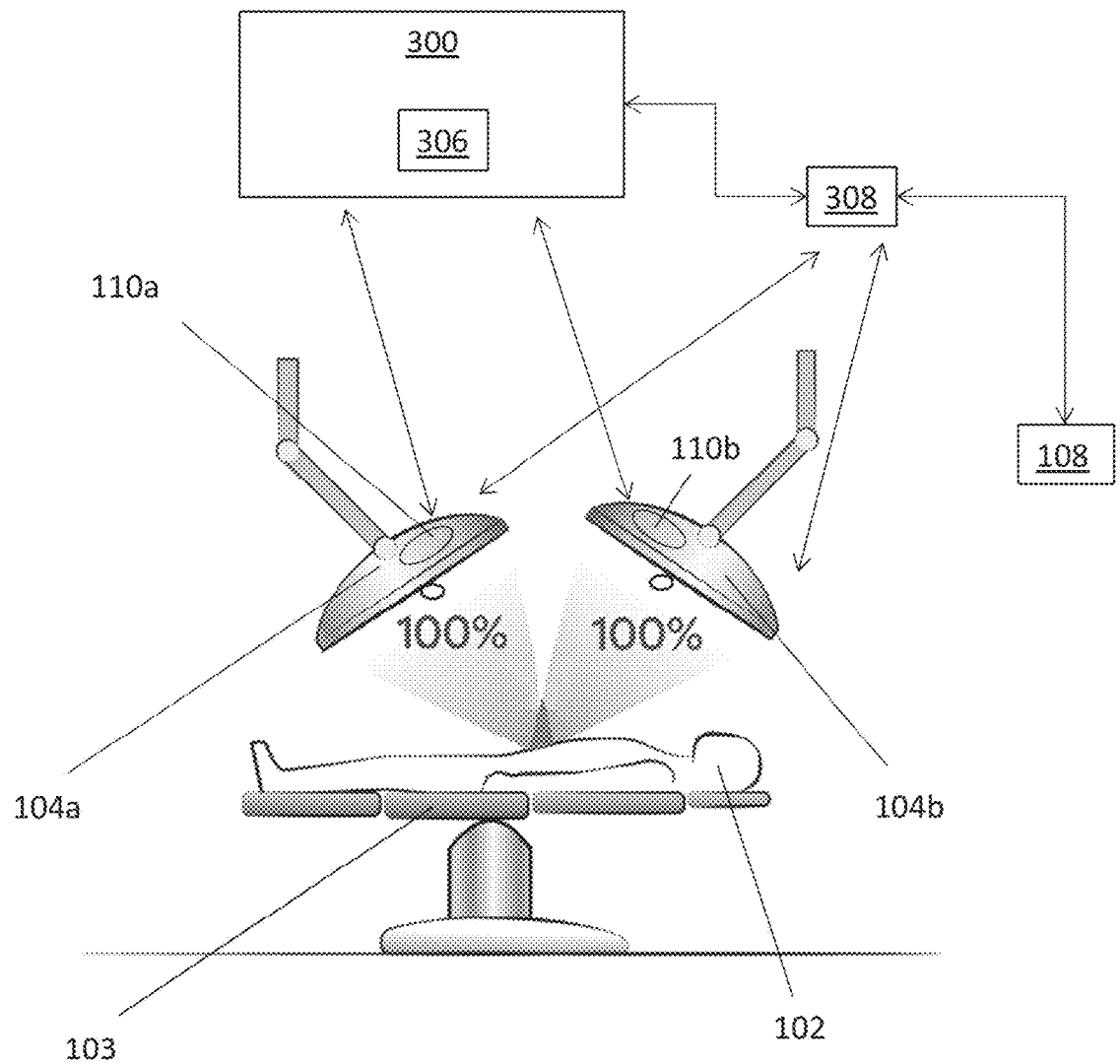
FIG. 3 shows a schematic illustration of a surgical lighting apparatus according to a third embodiment, including an indication system according to a third embodiment.

As shown in FIG. 3, a further example of an indication system 300 comprises the computer device 306 which is in communication with each of the light modules 104a, 104b, and also in communication with a controller 308 which is in communication with the wall control panel 108. As can be seen, the controller 308 is also in communication with each of the light modules 104a, 104b. The controller 308 is configured to receive inputs from the wall control panel 108, or from the light module control panels 110a, 110b, and then issue corresponding commands to the light modules 104a, 104b to control their illumination outputs. As will be appreciated, the controller 308 may be provided as a stand-alone device as shown in FIG. 3, or as part of one or more of the light modules 104a, 104b, as part of the indication system 300, or as part of the wall control panel 108.

Figure 4:
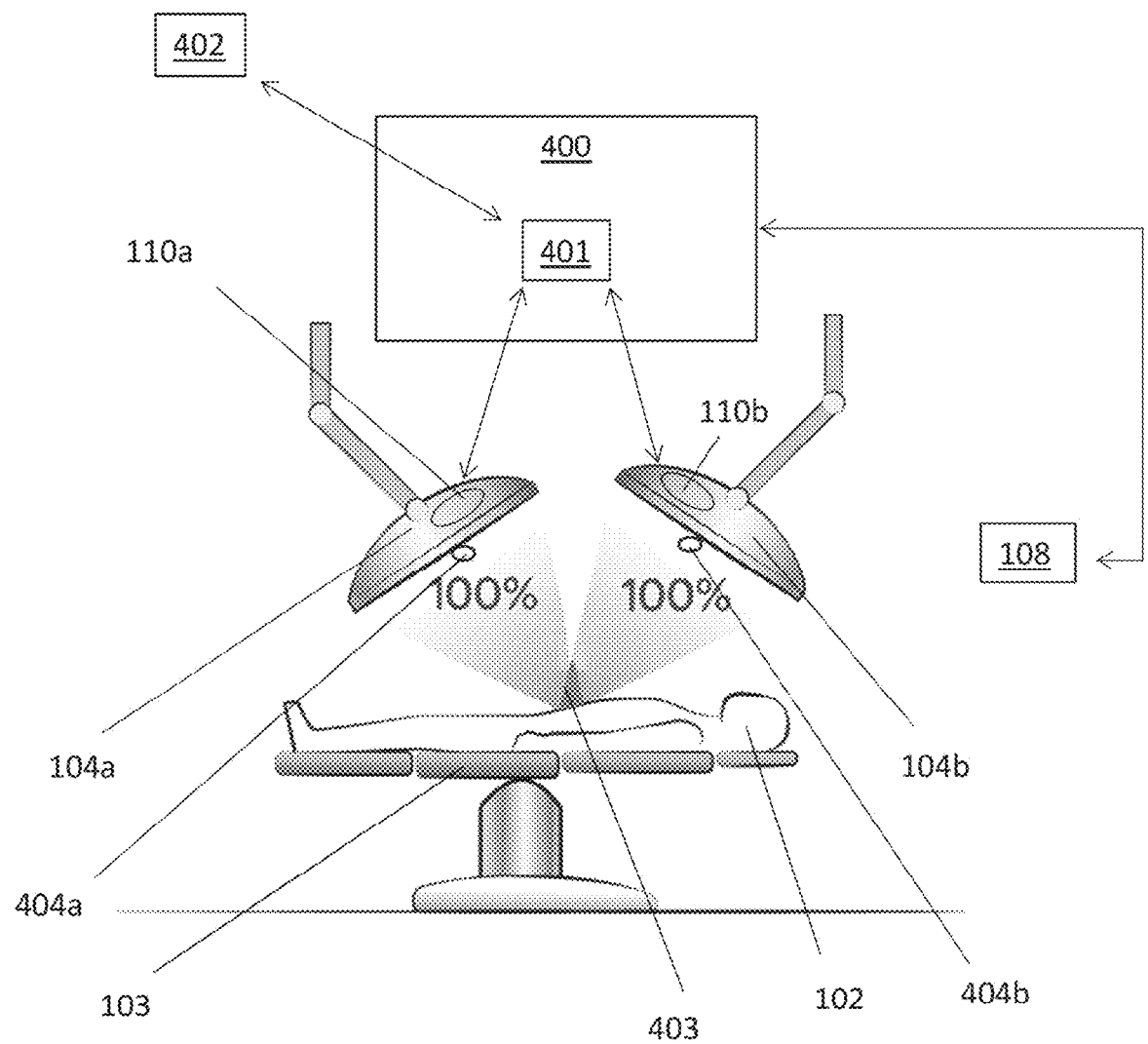
FIG. 4 shows a schematic illustration of a surgical lighting apparatus according to a fourth embodiment, including an indication system according to a fourth embodiment.

As shown in FIG. 4, a further example of an indication system 400 comprises computer device 401. The indication

TABLE 1 illumination settings for a first light module (LH1), a second light module (LH2), and a third light module (LH3) for surgical lighting apparatuses having one (1 LH), two (2 LH), or three (3 LH) light modules, a combined illumination setting of the two light modules having the two highest illumination settings (2 LHmax), and whether an indication is output.

|  | LH1 | | LH2 | | LH3 | | SUM | (2 LH$_{max}$) | Notification |
|---|---|---|---|---|---|---|---|---|---|
| 1LH | 100% | 160 klx | 0% | 0 klx | 0% | 0 klx | 100% | 160 klx | Disabled |
| 2LH | 50% | 80 klx | 50% | 80 klx | 0% | 0 klx | 100% | 160 klx | Disabled |
|  | 80% | 128 klx | 50% | 80 klx | 0% | 0 klx | 130% | 208 klx | Disabled |
|  | 80% | 128 klx | 80% | 128 klx | 0% | 0 klx | 160% | 256 klx | Output |
| 3LH | 50% | 80 klx | 50% | 80 klx | 50% | 80 klx | 100% | 160 klx | Disabled |
|  | 80% | 128 klx | 50% | 80 klx | 50% | 80 klx | 130% | 208 klx | Disabled |
|  | 80% | 128 klx | 50% | 80 klx | 80% | 128 klx | 160% | 256 klx | Output |

Alternatively, the illumination settings of each of the light modules 104a, 104b may be individually compared to different output illumination thresholds. For example, the illumination setting of the first light module 104a may be system 400 operates in a similar manner to indication systems 100 and 300 described above. However, indication system 400 is further connected to a detection system 402. The detection system 402 is configured to detect if illumination zones of the light modules 104a, 104b overlap. As shown in FIG. 4, the illumination zones may overlap in an overlapping region 403. The detection system 402 receives data from cameras 404a, 404b, in particular structured light cameras/systems, provided in each of the light modules 104a, 104b. Such a light module is marketed by Trumpf Medizin Systeme GmbH as iLEDTM 7.

Alternatively, the cameras 404a, 404b may be standard cameras, such as RGB cameras using a CCD or CMOS type sensor.

Figure 5:
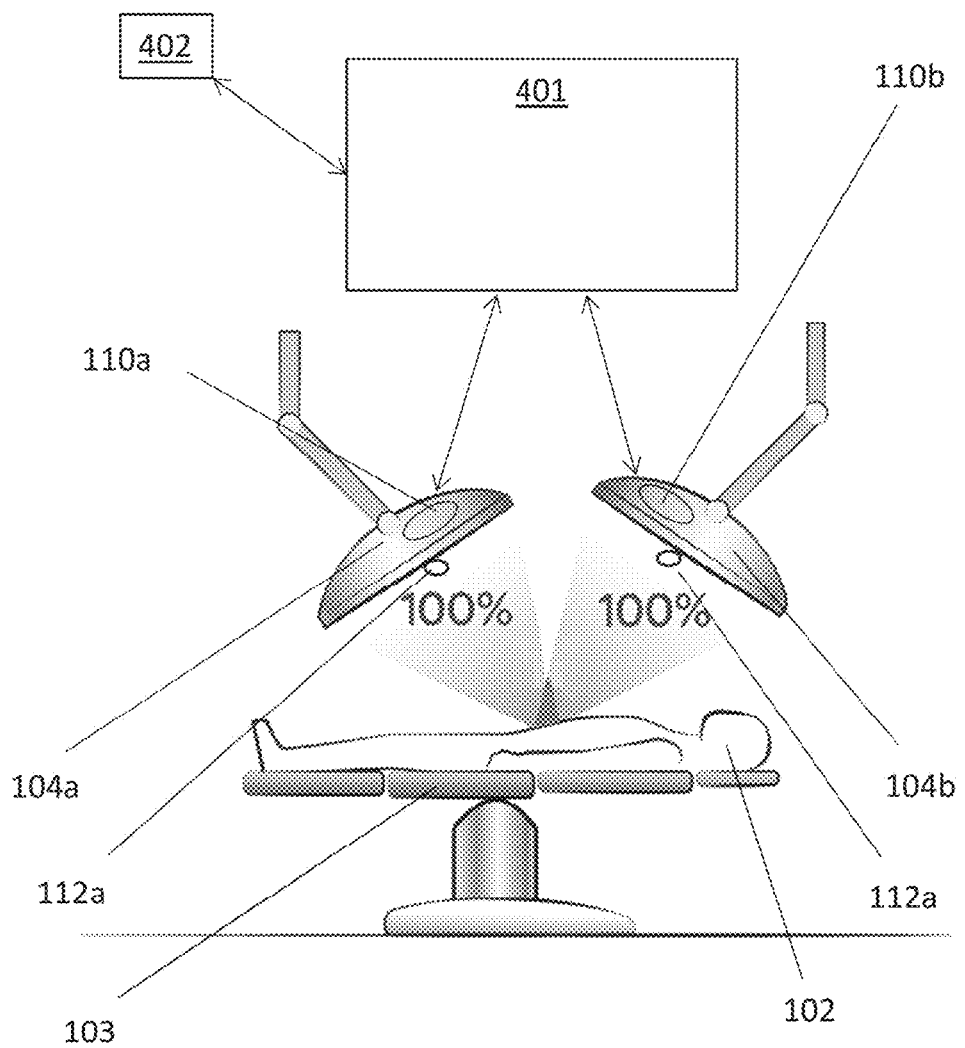
FIG. 5 shows a schematic illustration of a surgical lighting apparatus according to a further embodiment, including a detection system according to an embodiment.

As shown in FIG. 5, the present disclosure also relates to a detection system 402 connected to, or comprising, a computer device 401, independent of the indication system 100 or 300.

Figure 6:
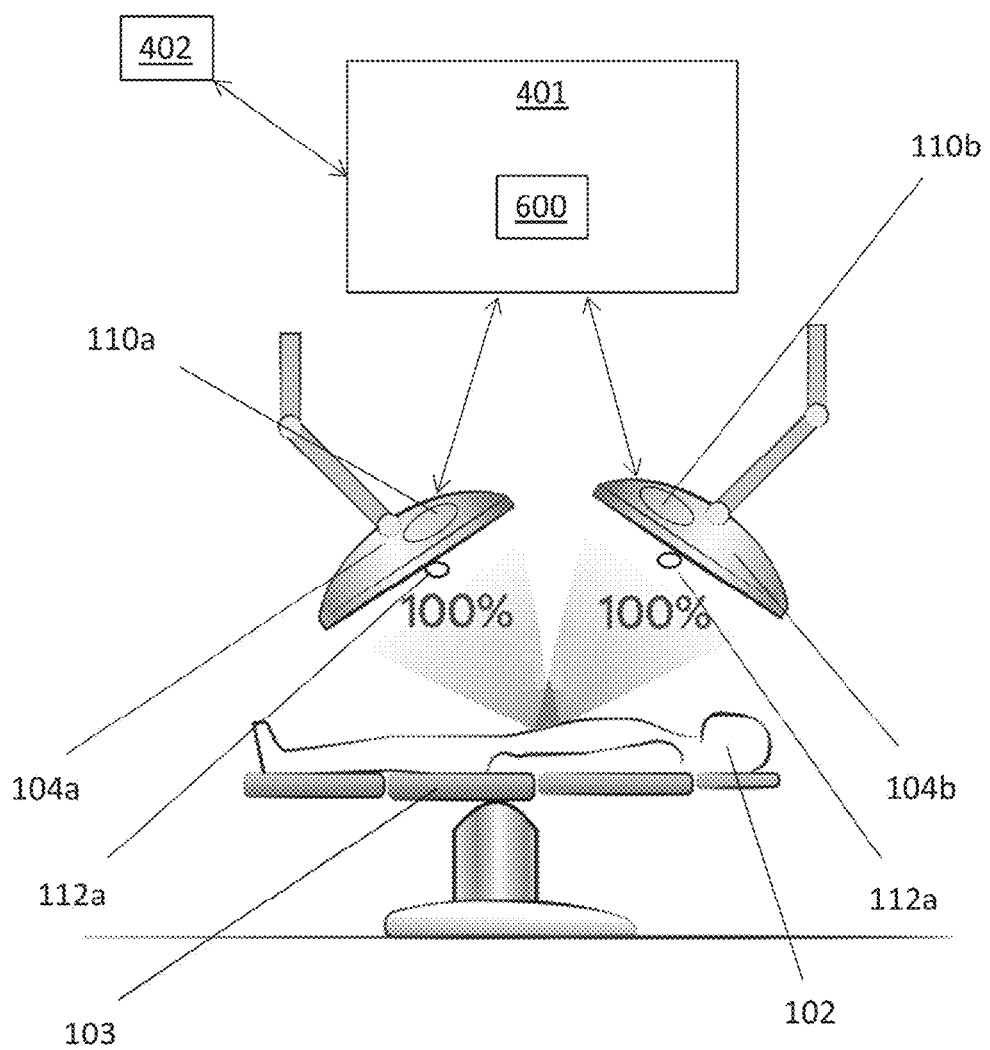
FIG. 6 shows a schematic illustration of a surgical lighting apparatus according to a yet further embodiment, including a detection system according to a further embodiment.

As shown in FIG. 6, the detection system 401, whether provided independently from the indication system 100 or 300, or together with, or as part of, the indication system 100 or 300, may further comprise, as part of the computer device 401, an artificial neural network 600.

Figure 7:
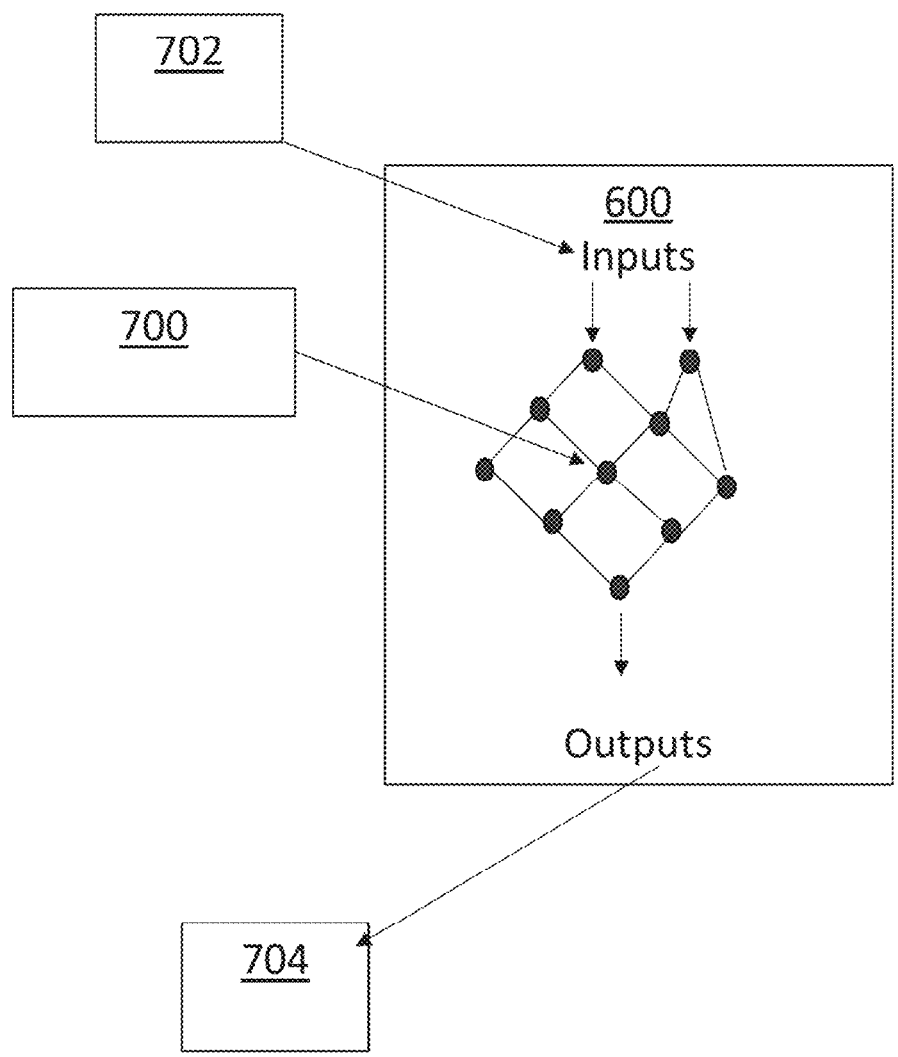
FIG. 7 shows a schematic illustration of a neural network of a detection system of a surgical lighting apparatus according to the yet further embodiment.
Figure 8:
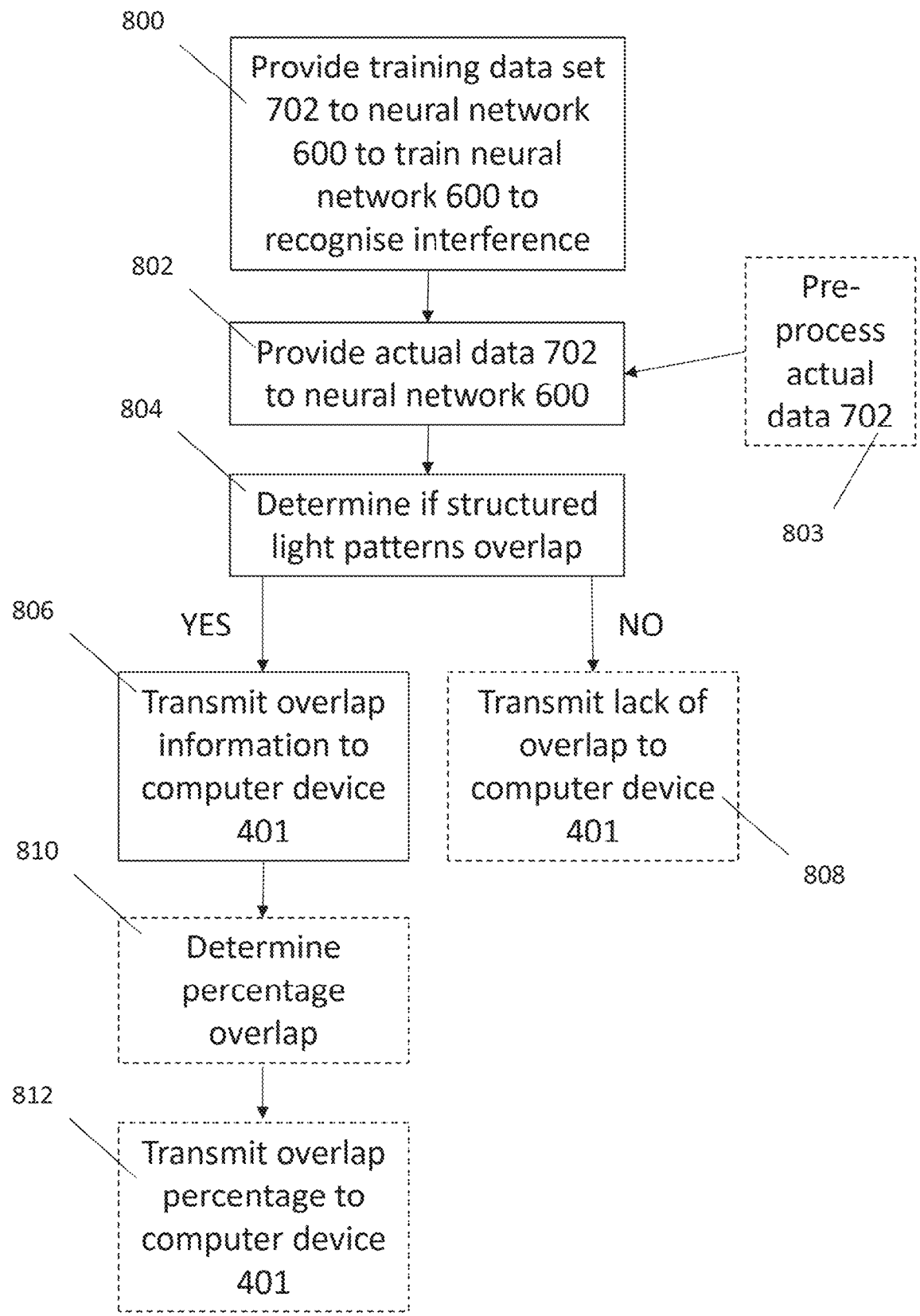
FIG. 8 shows a flow diagram of use of the neural network of FIG. 7.

As shown in FIGS. 7 and 8, the artificial neural network 600 may be trained using a training data set 700. The training data set 700 may comprise labelled data, wherein the labelled data includes pairs consisting of an input and a desired output. Upon training using the training data set 700, each node layer in the neural network 600 is configured to automatically learn to recognise features of the training data set 700 by repeatedly trying to reconstruct the input (i.e. the training data set). The neural network 600 learns by trying to minimize the difference between the network's outputs and the probability distribution of the training data set 700. The training data set 700 may be generated in conditions which are close to real conditions, i.e. conditions during use.

The labelled data of the training data set 700 may comprise inputs such as images from cameras, e.g. structured light images from structured light systems, or RGB images from standard cameras. While this example relates to supervised machine learning to generate the neural network 600, the skilled person would understand that, where appropriate, semi-supervised machine learning, or other machine learning may be used.

Once the neural network 600 has been trained, actual data 702, such as data from the structured light cameras 404a, 404b, is used as inputs, and the output may be whether there is an overlap 704 of the illumination zones of the light modules 104a, 104b. The output may further include a percentage of the overlap 704.

If the actual data 702 is data from structured light cameras 404a, 404b, the neural network 600 may be configured to recognise interference between structured light patterns of the structured light cameras 404a, 404b.

Alternatively, if the cameras 404a, 404b are standard cameras such as RGB cameras, the neural network 600 may be trained using data from the RGB cameras. If the actual data 702 is data from RGB cameras, the neural network 600 may be configured to recognise corresponding features, i.e. features present in the images of different RGB cameras. If the same features are detected in images of different RGB cameras, overlap may be recognised.

The neural network 600 may be developed using an open source machine learning platform such as TensorFlow, or PyTorch.

As set out in FIG. 8, the neural network 600 is provided 800 with a training data set 702 to train the neural network 600 to recognise interference of structured light patterns. The trained neural network 600 is then provided 802 with actual data.

The actual data may be pre-processed 803 to facilitate processing of the actual data by the neural network 600. For example, the actual data may be pre-processed 803 by at least one of: cropping the input structured light images or RGB images; and reducing a resolution of the input structured light images or RGB images to increase the performance of overlap detection. Cropping the input may include cropping the input to correspond to the portion of the input corresponding to the corresponding illumination zone.

The actual data 702, or the pre-processed actual data 702 if the actual data 702 is pre-processed in step 803, is processed by the neural network 600 to determine 804 if the structured light patterns of the structured light cameras 404a, 404b overlap. The structured light pattern produced by the structured light cameras may be configured to cover the entire illumination zone of the respective light module 104a, 104b so that any overlap in structured light pattern means that the illumination zones of the light modules 104a, 104b must also be overlapping.

If interference is found, i.e. if it is found that the structured light patterns overlap, the information that the light patterns overlap is transmitted 806 to the computer device 401. If no interference is found, i.e. it is found that the structured light patterns do not overlap, the information that the light patterns do not overlap may be transmitted 806 to the computer device 401.

If interference is found, the neural network 600 may be trained, and configured, to determine 810 a percentage overlap of the structured light patterns. The overlap percentage may be transmitted 812 to the computer device 401. The percentage overlap, if the training and actual data is from RGB cameras, may also be determined using corresponding features from feature detection.

The overlap percentage may be taken into account when determining if an indication is output. For example, the indication may only be output if the overlap percentage is greater than 10%, or greater than 20%, or greater than 30%.

Alternatively or additionally, if the illumination setting is to be automatically reduced after the at least one output illumination threshold is exceeded for a predetermined period of time and/or by a predetermined illumination setting amount and/or upon the indication not being acknowledged within a predetermined period of time, the predetermined period of time may be decreased, and the predetermined illumination setting amount may be decreased, upon the level of overlap increasing. That is to say, the predetermined period of time is shortest, and the predetermined illumination setting amount is lowest, upon the level of overlap being 100%; there being a direct relationship between the increase in the predetermined period of time, or the increase in the predetermined illumination setting amount, and the reduction in the level of overlap.

The neural network 600 may be configured to continue training after the initial training with the training data set 700. For example, intermittently, the neural network 600 may request confirmation that the result of overlap detection (i.e. existence of overlap, percentage of overlap, or lack of overlap) is correct. Additionally or alternatively, the neural network 600 may be intermittently provided with additional training data, comprising pairs of inputs and desired outputs, to improve the neural network 600.

Figure 9A:
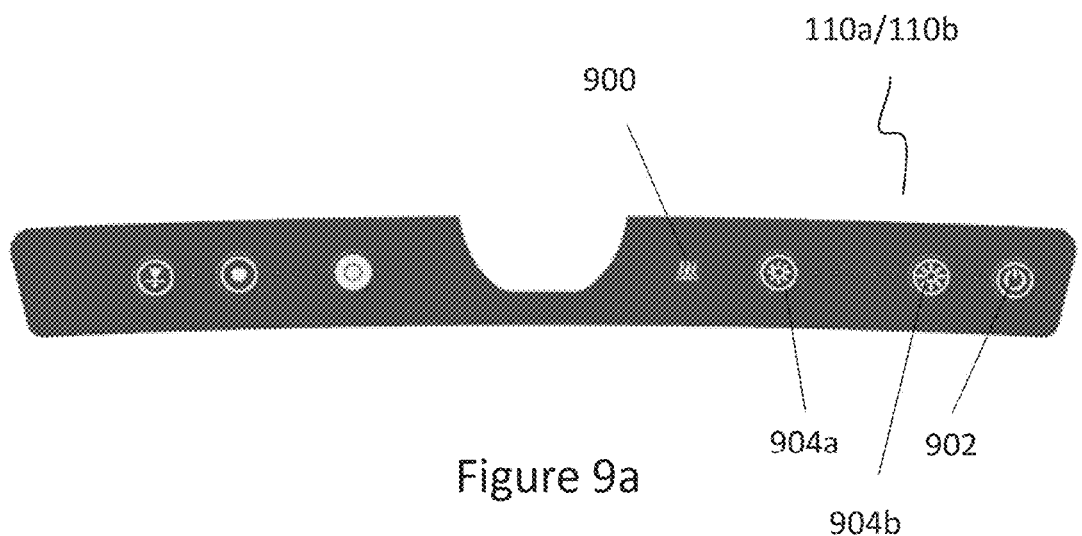
FIGS. 9a, 9b, and 9c show example light module control panels for a surgical lighting apparatus, or an indication system, according to one of the embodiments.

FIG. 9a shows an example of the light module control panel 110a, 110b of the light modules 104a, 104b having an icon 900 which may be illuminated to output the indication. In some embodiments, the icon 900 may be a button which may be pressed to acknowledge the indication. However, generally, if an illumination setting is changed using a light module control panel 110a, 110b, no acknowledgement of the indication should be required.

The light module control panel 110a, 110b further comprises an input, in the form of a button 902, to switch the light module 104a, 104b between on and off, and inputs, in the form of buttons 904a, 904b, for increasing and decreasing the illumination setting of the light module 104a, 104b.

Figure 9B:
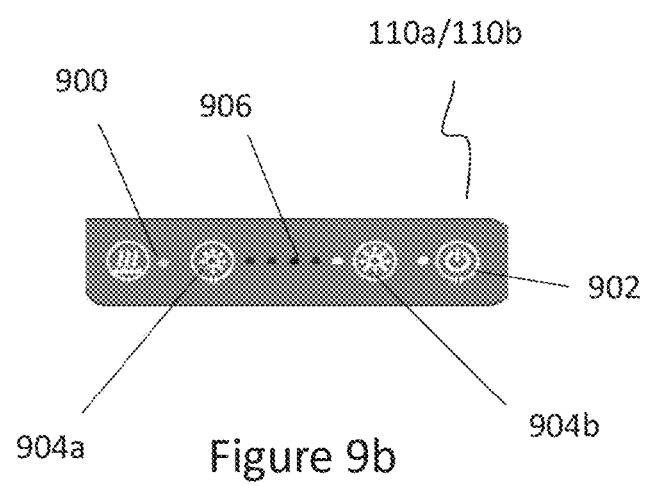
Figure 9C:
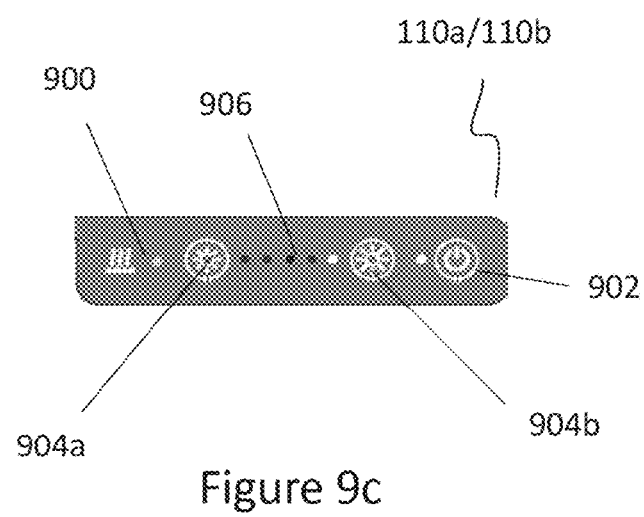

FIGS. 9b and 9c show further examples of the light module control panel 110a, 110b, wherein instead of the indication icon 900 being illuminated, a light adjacent the icon may be illuminated to output the indication. The light module control panels 110a, 110b may further comprise an illumination setting indicator 906, which comprises a number of indicia to indicate a current illumination setting of the light module 104a, 104b.

Figure 10A:
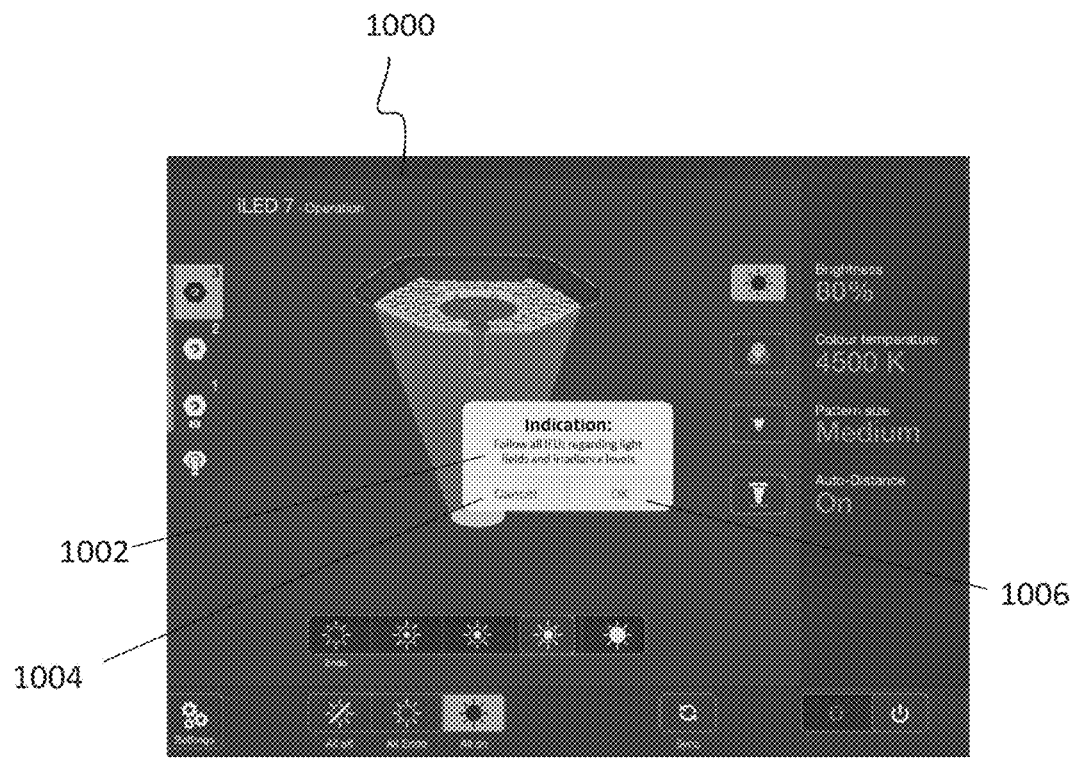
FIGS. 10a and 10b show example Graphical User Interfaces (GUIs) for a surgical lighting apparatus, or an indication system, according to one of the embodiments.
Figure 10B:
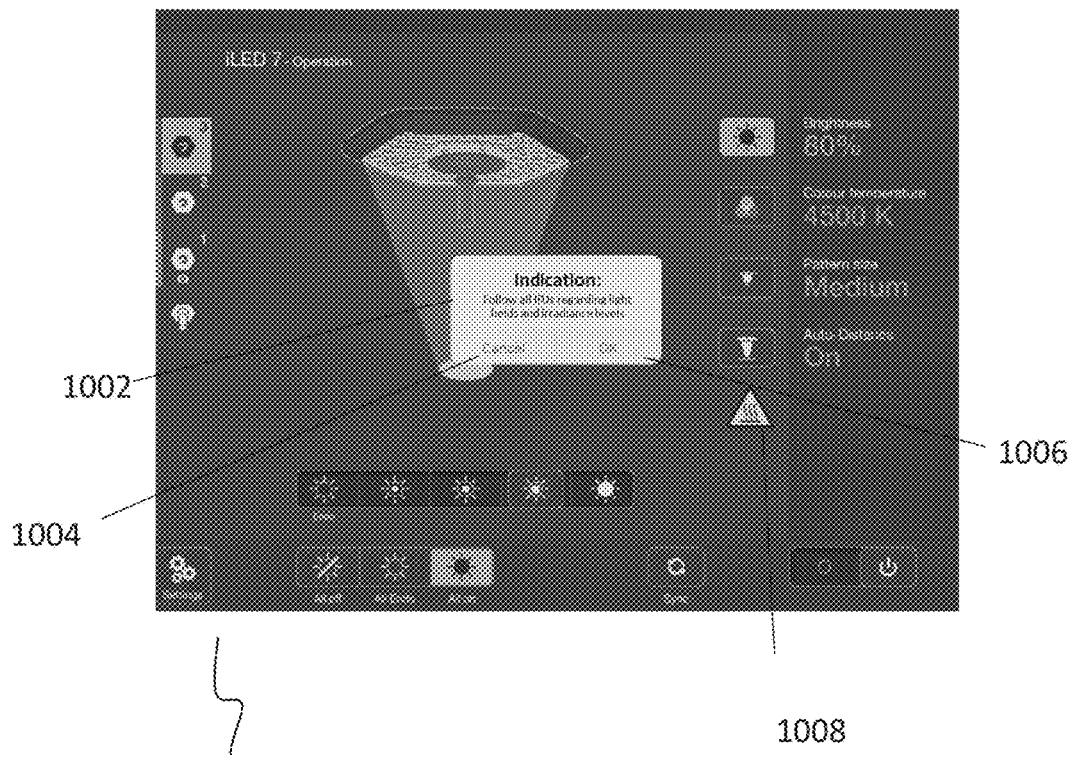

FIGS. 10a and 10b show examples of Graphical User Interfaces (GUI) 1000 for outputting the indication. The GUI may be displayed on the wall control panel 108 and/or on a third party device such as a tablet.

The indication may be displayed within the GUI 1000 as a pop-up window 1002. The pop-up window 1002 may include one or more buttons for acknowledging the indication. In the embodiments of FIGS. 10a and 10b, the GUI comprises a "Cancel" button 1004 which may cause an automatic reduction in the illumination setting of at least one of the light modules 104a, 104b, or may simply cause removal of the indication, and an "OK" button 1006 which only acknowledges the indication, and may cause the requested increase in the illumination setting to be initiated.

In addition, the pop-up window 1002 may provide a link, such as a hyperlink, to the relevant instructions for use (IFUs), and in particular the link may be to the particular page or section in the relevant instructions for use. On initiation of the link a further pop-up window (not shown) may be provided with the relevant instructions for use for immediate review by the user. Alternatively, on initiation of the link, the system may provide access to the relevant instructions for use using the standard user interface for the instructions for use.

In addition to the pop-up window 1002, FIG. 10b of the example GUI 1000 shows an example of an additional indicator 1008, which may be displayed to draw further attention to the indication. Even after acknowledgement of the indication pop-up window 1002, the additional indicator 1008 may still be displayed in the GUI 1000.

The indication may be displayed on more than one of the light module control panel 104a, 104b, a third party device, and the wall control panel 108.

It will be appreciated that the above described embodiments are illustrative embodiments of the disclosure only. It will also be appreciated that features described above in relation to one embodiment of the disclosure may also be applied to other embodiments of the disclosure.

While the disclosure has been illustrated and described in detail in the drawings and the foregoing description, such illustration and description are to be considered illustrative and not restrictive. The disclosure is not limited to the disclosed embodiments. From reading the present disclosure, other modifications will be apparent to a person skilled in the art. Such modifications may involve other features, which are already known in the art and may be used instead of or in addition to features already described herein. In the claims, the word "comprising" does not exclude other elements or steps, and the indefinite article "a" or "an" does not exclude a plurality.

The invention claimed is:

1. An indication system for a surgical lighting apparatus, comprising:
   a computer device connectable to a plurality of light modules, wherein the computer device is configured to:
   determine an illumination setting for each of the plurality of light modules;
   compare the illumination settings of at least two of the plurality of light modules to at least one output illumination threshold; and,
   output an indication if the at least one output illumination threshold is exceeded;
   wherein the computer device is configured to:
   if the plurality of light modules comprises more than two light modules, determine the two of the plurality of light modules having the two highest illumination settings.

2. An indication system according to claim 1, wherein the step of comparing the illumination settings of at least two of the plurality of light modules to at least one output illumination threshold comprises:
   combining the illumination settings of the at least two of the plurality of light modules, or of the two of the plurality of light modules having the two highest illumination settings, and comparing the combined illumination setting to a total output illumination threshold.

3. An indication system according to claim 1, wherein the indication is at least one of:
   a visual indication; and
   an audible indication.

4. An indication system according to claim 1, wherein the indication is output on at least one of:
   one of the plurality of light modules;
   a wall control panel;
   a mobile controller; and
   a third party device.

5. An indication system according to claim 1, wherein the indication comprises context-sensitive information regarding at least one of:
   a patient characteristic;
   surgery type;
   environmental data;
   illumination settings, and/or focus settings, of the at least two light modules.

6. An indication system according to claim 1, wherein the computer device is configured to receive at least one of:
   inputs for acknowledging the indication;
   inputs for putting the indication system on hold; and
   inputs for delaying the indication.

7. A surgical lighting apparatus comprising:
   an indication system according to claim 1; and
   a plurality of light modules connected to the computer device.

8. A surgical lighting apparatus according to claim 7, wherein each of the plurality of light modules comprises a structured light camera connected to the computer device.

9. A surgical light apparatus according to claim 7, wherein each one of the plurality of light modules comprises at least one of:
   a position sensor;
   an angle sensor;
   an accelerometer; and
   a gyroscope, each configured to be used in determining whether an illumination zone of one of the plurality of light modules overlaps with an illumination zone of another one of the plurality of light modules.

10. An indication system for a surgical lighting apparatus, comprising:
a computer device connectable to a plurality of light modules, wherein the computer device is configured to:
determine an illumination setting for each of the plurality of light modules;
compare the illumination settings of at least two of the plurality of light modules to at least one output illumination threshold; and,
output an indication if the at least one output illumination threshold is exceeded; wherein the step of comparing the illumination settings of at least two of the plurality of light modules to at least one output illumination threshold comprises:
comparing an illumination setting of a first one of the plurality of light modules to a first output illumination threshold, and an illumination setting of a second one of the plurality of light modules to a second, dynamic, output illumination threshold, the second threshold being dependent on at least one of the first threshold and the first illumination setting.

11. An indication system for a surgical lighting apparatus, comprising:
a computer device connectable to a plurality of light modules, wherein the computer device is configured to:
determine an illumination setting for each of the plurality of light modules;
compare the illumination settings of at least two of the plurality of light modules to at least one output illumination threshold; and,
output an indication if the at least one output illumination threshold is exceeded;
wherein the computer device is configured to, if the plurality of light modules comprises more than two light modules, determine the two of the plurality of light modules having the two highest illumination settings; and wherein the step of comparing the illumination settings of at least two of the plurality of light modules to at least one output illumination threshold comprises:
comparing an illumination setting of a first one of the plurality of light modules to a first output illumination threshold, and an illumination setting of a second one of the plurality of light modules to a second, dynamic, output illumination threshold, the second threshold being dependent on at least one of the first threshold and the first illumination setting;
and, wherein the first one and the second one of the plurality of light modules are the two of the plurality of light modules having the two highest illumination settings.

12. An indication system for a surgical lighting apparatus, comprising:
a computer device connectable to a plurality of light modules, wherein the computer device is configured to:
determine an illumination setting for each of the plurality of light modules;
compare the illumination settings of at least two of the plurality of light modules to at least one output illumination threshold; and,
output an indication if the at least one output illumination threshold is exceeded;
wherein the computer device is configured to determine whether an illumination zone of one of the plurality of light modules overlaps with an illumination zone of another one of the plurality of light modules, and
wherein the computer program is configured:
not to output the indication if the illumination zones do not overlap; and/or
to output a further indication if the illumination zones do overlap and the output illumination threshold is exceeded; and/or
to output the indication only if the illumination zones overlap;
wherein the computer device is configured to determine a percentage overlap if the illumination zones overlap.

13. An indication system for a surgical lighting apparatus, comprising:
a computer device connectable to a plurality of light modules, wherein the computer device is configured to:
determine an illumination setting for each of the plurality of light modules;
compare the illumination settings of at least two of the plurality of light modules to at least one output illumination threshold; and,
output an indication if the at least one output illumination threshold is exceeded;
wherein the computer device is configured to determine whether an illumination zone of one of the plurality of light modules overlaps with an illumination zone of another one of the plurality of light modules, and
wherein the computer program is configured:
not to output the indication if the illumination zones do not overlap; and/or
to output a further indication if the illumination zones do overlap and the output illumination threshold is exceeded; and/or
to output the indication only if the illumination zones overlap;
wherein each one of the plurality of light modules comprises at least one of:
a structured light system, and wherein the step of determining whether the illumination zones overlap comprises detecting an interference pattern of structured light of the structure light systems; and
a camera, and the step of determining whether the illumination zones overlap comprises comparing images of each of the cameras for corresponding features.

14. An indication system according to claim 13, wherein the computer device comprises an artificial neural network, configured using a training set of data, wherein:
the step of detecting the interference pattern comprises using the artificial neural network to detect the interference pattern of the structured light; and/or
the step of comparing images of each of the cameras for corresponding features comprises using the artificial neural network to detect if the same feature or features are present in images of different cameras.

15. An indication system according to claim 14, wherein the artificial neural network being configured to receive and process context-sensitive information based on at least one of:
a patient characteristic;
surgery type;
environmental data; and
illumination settings, and/or focus settings, of the at least two light modules.

16. A method of indication for a surgical lighting apparatus comprising at least three light modules, comprising:

determining an illumination setting for each of the light modules; comparing the illumination settings of at least two of the light modules to at least one output illumination threshold; and outputting an indication in response to the at least one output illumination threshold being exceeded.

17. The method of indication for a surgical light apparatus according to claim 16 comprising combining the illumination settings of the at least two of the light modules, or the two light modules having the two highest illumination settings, and comparing the combined illumination setting to a total output illumination threshold.

* * * * *